United States Patent [19]

Szüts et al.

[11] Patent Number: 4,670,440
[45] Date of Patent: Jun. 2, 1987

[54] MEDICINAL NORFLOXACIN SALTS

[75] Inventors: Tamás Szüts; Péter Szentmiklósi; József Lengyel; István Hermecz; Lelle Vasvári née Debreczy; Ágnes Horváth; Géza Kerszturi; Gábor Kovács; Gábor Horváth, all of Budapest; Katalin Mármarosi née Kellner, Biatorbágy, all of Hungary

[73] Assignee: Chinoin Gyogyszer es Vegyeszeti Termekek Gyara RT., Budapest, Hungary

[21] Appl. No.: 854,395

[22] Filed: Apr. 21, 1986

[30] Foreign Application Priority Data

Apr. 29, 1985 [HU] Hungary ............................. 1634/85

[51] Int. Cl.$^4$ .................. A61K 31/495; C07D 401/04
[52] U.S. Cl. ..................................... 514/254; 544/363
[58] Field of Search ......................... 544/363; 514/254

[56] References Cited

U.S. PATENT DOCUMENTS

| 4,442,101 | 4/1984 | Ichihashi et al. | 544/363 |
| 4,455,310 | 6/1984 | Sakamoto et al. | 544/363 |
| 4,472,579 | 9/1984 | Irikura et al. | 544/363 |
| 4,522,819 | 6/1985 | Fox, Jr. et al. | 544/363 |

OTHER PUBLICATIONS

Fox, Jr. et al. (II), "Chemical Abstracts", vol. 97, 1982, col. 97:78883n.
Mich, "Chemical Abstracts", vol. 98, 1983, col. 98:149589e.
Grohe et al., "Chemical Abstracts", vol. 103, 1985, col. 103:92841w.

Primary Examiner—Glennon H. Hollrah
Assistant Examiner—James H. Turnipseed
Attorney, Agent, or Firm—Karl F. Ross; Herbert Dubno; Jonathan Myers

[57] ABSTRACT

N,N,N-trimethyl-2-hydroxyethyl-ammonium-[1-ethyl-6-fluoro-4-oxo-7-(1-piperazinyl)-1,4-dihydro-quinolizine-3-carboxylate] of the formula I

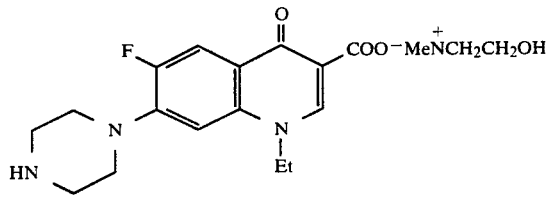

as a norfloxacin antimicrobial salt capable of enteral administration.

5 Claims, No Drawings

MEDICINAL NORFLOXACIN SALTS

FIELD OF THE INVENTION

The present invention relates to the new salts of 1-ethyl-4-oxo-6-fluoro-7-(1-piperazinyl)-1, 4-dihydro-quinoline-3-carboxylic acid (norfloxacin) formed with N,N,N-trimethyl-2-hydroxy-ethyl-ammonium hydroxide,

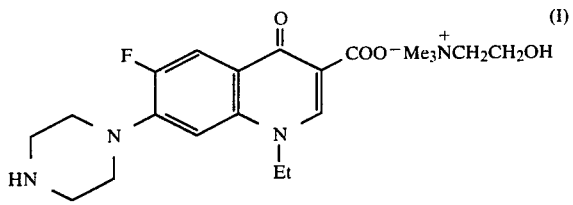

to the preparation thereof and compositions containing same. Norfloxacin (Belgian Pat. No. 863,429) is the first of the nalidixic acid analogs of generation III, which has good activity in the therapy of urethral infections caused by Pseudomonas aeruginosa and gram positive and gram negative bacteria. (Antimicrobial Agents and Chemotherapy 1980, 17, 103–108).

BACKGROUND OF THE INVENTION

It is known that norfloxacin is not absorbed well by the organism due to its low watersolubility (0.20 mg/ml) (J. Antimicr. Chemother. 1984, 13, suppl. $B_1$, 66); therefore the therapeutic blood level develops slowly. Going through the intestines only about 40% of the material is absorbed because of the low solubility.

DESCRIPTION OF THE INVENTION

It has been found that the solution necessary for absorption forms quickly when the N,N,N-trimethyl-2-hydroxymethylammonium hydroxide salt is formed according to the invention, thereby resulting in better absorption. The watersolubility of the new compound of the Formula I according to the invention, i.e. N,N,N-trimethyl-2-hydroxyl-ethyl-ammonium [-1-ethyl-6-fluoro-4-oxo-7-(1-piperazinyl)-1,4-dihydro-quinoline-carboxylate] is more than 1 g/ml. The quick absorption and the good biological utilization enable reduction of the dosage needed for the therapeutic effect, and hence to a reduction of side effects. While—because of the slow and bad absorption and the quick evacuation no sustained release form for norfloxacin was previously developed, the excellent absorption of the compound according to the invention makes even this dosage form possible.

In case of a body weight of 70 kg. the composition according to the invention can be administered in a dose ranging from 70 mg. to 15 g., preferably from 200 mg. to 5 g., per day in divided dosages. The compound of the formula I is suitable for human therapy in the form of tablets, capsules, dragees, enterosoluble dragees, suppositories, solutions, syrups, or in a sustained release form of any of these. The pharmaceutical compositions can be prepared by methods known per se in the pharmacological industry.

In veterinary therapy the active ingredient of the Formula I can be applied, in addition to the forms used in human therapy, also as the free active ingredient admixed with the food of the animals in any form or as food additive.

The compound of the Formula I can be readily prepared by reacting 1-ethyl-6-fluoro-4-oxo-7-(1-piperazinyl)-1,4-dihydro-quinoline-3-carboxylic acid with N,N,N-trimethyl-2-hydroxyethyl-ammonium hydroxide in an aqueous or alcoholic or aqueous-alcoholic medium. As alcohols $C_{1-4}$ straight or branched chained aliphatic alcohols, preferably methylalcohol, ethylalcohol, isopropanol can be used. The compound of the Formula I can be isolated by usual methods, e.g. optionally by evaporation at low pressure or lyophilization. Optionally the obtained compound of the Formula I can be crystallized.

Further details of the invention are shown in the following examples.

EXAMPLE 1

Preparation of N,N,N-trimethyl-2-hydroxyethyl-ammonium-[1-ethyl-6-fluoro-4-oxo-7-(1-piperazinyl)-1,4-dihydro-quinoline-3-carboxylate].

In a round-bottomed 1000 ml. flask 20 g. of 1-ethyl-4-oxo-6-fluoro-7-(piperazinyl)-1,4-dihydro-quinoline-3-carboxylic acid are suspended in a mixture of 150 ml. methanol and 50 ml. distilled water. From a dropping funnel 18 ml. of N,N,N-trimethyl-2-hydroxyethyl-ammonium hydroxide (choline base) dissolved in 50% methanol are added dropvise to the suspension under constant stirring at room temperature. A clear, light yellow solution is obtained. The aqueous-methanolic solution is evaporated above 40% water bath in vacuo. The yellow, adhesive solution thus obtained is suspended in 200 ml of acetone and heated to boiling, then isopropanol (36 ml.) is added dropwise under boiling until total dissolution. The solution is cooled slowly. The precipitated material is filtered under vacuo on a glass filter G-4 and washed. Wet-weight after filtration: 27.4 g.

The wet material is dried for 20 hours above $P_2O_5$ in a vacuum desiccator.

Dry-weight: 24.6

Meltingpoint: 102°–104° C.

The remaining isopropanol is removed by drying for 3 hours at 70° C. in a desiccator.

Obtained material: 23.9 g (90.4%).

Melting point: 130°–132° C.

Analysis for the formula $C_{21}H_{32}N_4O_4F$: Calculated: C 59.56%, H 7.62%, N 13.23%, F 4.49%, Found: C 59.72%, H 7.54%, N 13.36%, F 4.61%.

TABLE I

Comparison of the solubility of norfloxacin complex with guanidine carbonate 2:1 and N,N,N—trimethyl-2-hydroxyethylammonium-[1-ethyl-6-fluoro-4-oxo-7-(1-piperazinyl)-1,4-dihydroquinoline-3-carboxylate] in distilled water of a temperature of 25° C.

| Compound | Solubility | | Solubility calculated on Norfloxacin | |
|---|---|---|---|---|
| | mg/ml | μMol/ml | mg/ml | μMol/ml |
| Norfloxacin | 0.20 | 0.63 | 0.20 | 0.63 |
| Complex of guanidin carbonate | 12.5 | 15.3 | 9.8 | 30.6 |
| Compound of the Formula I | >1000 | >2360 | >753 | >2360 |

1 = EP PS 84011

EXAMPLE 2

In in vitro tests with agar-diffusion technique the minimal inhibiting concentration was determined (MIC) by series diluting method against the strains in the Table. Norfloxacin was dissolved in dimethyl-sulphoxide and the norfloxacin-THA salt was dissolved in water.

TABLE

| | MIC value (μg/ml) | | |
| --- | --- | --- | --- |
| Compound | E. Coli | Pseudomonas Aeruginosa | Staphylococcus aureus |
| Norfloxacin | 0.25–0.5 | 0.5–0.75 | 0.25–0.5 |
| Norfloxacin-THA-salt | 0.05–0.25 | 0.25–0.5 | 0.25 |

EXAMPLE 3

Formulating examples a. Composition of the tablets with an active ingredient content of 100–400 mg.

| (calculated on 100 tablets) | |
| --- | --- |
| Compound of the Formula I | 10.0–40.0 g. |
| Lactose | 2.0 g. |
| Saccharose | 0.3 g. |
| Amylum solani | 5.2 g. |
| Mucilago ad gran. | q.s |
| Magn. stearat | 0.1 g. |
| Talcum | 0.2 g. |
| Amylum solani ad | 60.0 g. |
| Composition of granulating solution | |
| Gelatin alba | 5.0% |
| Amylum solani | 5.0% |
| Aqua dest. ad | 100.0% | b. Intestinosolvent dragees:

The dragees of the above composition are coated with Eurdragit L by methods known per se.

c. Composition of tablets with prolonged effect with an active ingredient content of 400 mg.

| (calculated on 100 tablets) | |
| --- | --- |
| Compound of the Formula I | 40.0 g. |
| CMC Na (Carboxy-methyl-cellulose-Na) | 4.5 g. |
| Lactose | 5.0 g. |
| Gypsum | 48.5 g. |
| Acid Stearinic | 5.0 g. |
| Aqua dest | q.s |
| Magn. stearinic | 0.7 g. |
| Talcum | 1.4 g. | d. Suppositories for children with an active ingredient content of 25–50 mg.

| (calculated on 100 suppositories) | |
| --- | --- |
| Compound of the Formula I | 2.5–5.0 g. |
| Tagat R 1 | 7.5 g. |
| Softisan 378 | 7.5 g. |
| Witopsol H 32 ad | 150.0 g. | e. Suppositories for adults with an active ingredient content of 100–400 mg.

| (calculated on 100 suppositories) | |
| --- | --- |
| Compound of the Formula I | 10.0–40.0 g. |
| Tagat R 1 | 15.0 g. |
| Softisan 378 | 15.0 g. |
| Witopsol H 32 ad | 300.0 g. |

We claim:

1. N,N,N-trimethyl-2-hydroxyethyl-ammonium-{1-ethyl-6-fluoro-4-oxo-7-(1-piperazinyl)-1,4-dihydro-quinolizine-3-carboxylate} of the formula

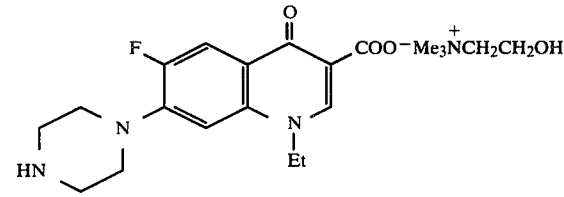

2. Pharmaceutical composition, comprising as active ingredient N,N,N-trimethyl-2-hydroxyethyl-ammonium-{1-ethyl-6-fluoro-4-oxo-7-(1-piperazinyl)-1,4-dihydro-quinolizine-3-carboxylate} and a pharmaceutically acceptable inert carrier.

3. Composition according to claim 2 for human and veterinary therapy which contains the active ingredient in the form of tablets, capsules, dragees, enterosolvent dragees, suppositories, solutions or syrup.

4. A method of veterinary therapy which comprises mixing or adding an antimicrobally effective amount of the active ingredient of claim 2 to the food of the animals.

5. An antimicrobial method of treatment which comprises administering enterally to an infected subject an effective amount of the compound defined in claim 1.

* * * * *